US009173842B2

(12) United States Patent
Paillard et al.

(10) Patent No.: US 9,173,842 B2
(45) Date of Patent: Nov. 3, 2015

(54) STABLE PHARMACEUTICAL COMPOSITION COMPRISING A HYDROSOLUBLE VINFLUNINE SALT

(75) Inventors: Bruno Paillard, Labege (FR); Jean-Louis Avan, Villefrance De Lauragais (FR); Joël Bougaret, Francarville (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 395 days.

(21) Appl. No.: 12/668,367

(22) PCT Filed: Jul. 9, 2008

(86) PCT No.: PCT/EP2008/058893
§ 371 (c)(1),
(2), (4) Date: Jan. 8, 2010

(87) PCT Pub. No.: WO2009/007388
PCT Pub. Date: Jan. 15, 2009

(65) Prior Publication Data
US 2010/0196468 A1    Aug. 5, 2010

Related U.S. Application Data

(60) Provisional application No. 60/970,334, filed on Sep. 6, 2007.

(30) Foreign Application Priority Data

Jul. 11, 2007  (FR) ...................... 07 56421

(51) Int. Cl.
A61K 9/16     (2006.01)
A61K 9/20     (2006.01)
A61K 9/28     (2006.01)
A61K 9/48     (2006.01)
A61K 31/4375  (2006.01)
A61K 31/4745  (2006.01)
A61K 31/475   (2006.01)

(52) U.S. Cl.
CPC ............ *A61K 9/1623* (2013.01); *A61K 9/1611* (2013.01); *A61K 9/1652* (2013.01); *A61K 9/2009* (2013.01); *A61K 9/2018* (2013.01); *A61K 9/2054* (2013.01); *A61K 31/4375* (2013.01); *A61K 31/475* (2013.01); *A61K 31/4745* (2013.01); *A61K 9/282* (2013.01); *A61K 9/284* (2013.01); *A61K 9/2846* (2013.01); *A61K 9/2866* (2013.01); *A61K 9/4866* (2013.01)

(58) Field of Classification Search
None
See application file for complete search history.

(56) References Cited

U.S. PATENT DOCUMENTS

| 5,620,985 | A | 4/1997 | Jacquesy et al. | |
|---|---|---|---|---|
| 6,127,377 | A | * 10/2000 | Duflos et al. | ............... 514/283 |
| 6,458,389 | B1 | 10/2002 | Debregeas et al. | |
| 2003/0224042 | A1 | 12/2003 | Bougaret et al. | |
| 2007/0155768 | A1 | 7/2007 | Leverd et al. | |
| 2007/0232533 | A1* | 10/2007 | Umezawa et al. | ............... 514/12 |

FOREIGN PATENT DOCUMENTS

| EP | 0147152 A2 | 7/1985 |
|---|---|---|
| EP | 1 623 986 A1 | 2/2006 |
| EP | 1764368 A1 | 3/2007 |
| FR | 2880274 A1 | 7/2006 |
| WO | WO-95/03312 A1 | 2/1995 |
| WO | WO 98/34599 A1 | 8/1998 |
| WO | WO 00/48571 A1 | 8/2000 |
| WO | WO 02/30427 A1 | 4/2002 |
| WO | WO 03/101383 A2 | 12/2003 |
| WO | WO-2005/070425 A1 | 8/2005 |
| WO | WO 2006/029579 A1 | 3/2006 |
| WO | WO 2006/040779 A2 | 4/2006 |
| WO | WO 2006/069938 A1 | 7/2006 |
| WO | WO-2007/071648 A1 | 6/2007 |
| WO | WO 2009/105937 A1 | 9/2009 |

OTHER PUBLICATIONS

Rowe et al., Handbook of Pharmaceutical Excipients, 2009, Pharm Press, 6th Ed., pp. 118-121, 129-133, 185-188, 326-329, 404-407,424-428, 858, 864, 865, 868 and 873.*
Gennaro A. R., Remington's Pharmaceutical Sciences, 1985, Mack Publishing, 17th Ed., p. 1625.*
Kavallaris at al., "Anticancer Therapy with Novel Tubulin-Interacting Drugs", Drug Resistance Updates, Dec. 2001, pp. 392-401, vol. 4. No. 6, XP009021226.
Fondation du Centre Pluridisciplinaire d'Oncologie, "Phase I Dose-Escalation Study of Vinflunin Hard Capsules Administered Once a Day from D1 to D5 and from D8 to D12 every 3 Weeks in Patients with Advanced/Metastatic Solid Tumors", Jun. 21, 2007, pp. 1-3, XP-002463736.
International Search Report dated Sep. 12, 2008 for International Application No. PCT/EP2008/058893.
Lush et al., "The absolute bioavailability of oral vinorelbine in patients with solid tumors," Cancer Chemother. Pharmacol., vol. 56, 2005, pp. 578-584, XP019334242.
Ribet et al., "Complete assignment of 1H and 13C NMR spectra of vinflunine," Magnetic Resonance in Chemistry, vol. 39, 2001, pp. 43-48.
Rowinsky et al., "Pharmacokinetic, Bioavailability, and Feasibility Study of Oral Vinorelbine in Patients With Solid Tumors," Journal of Clinical Oncology, vol. 12, No. 9, Sep. 1994, pp. 1754-1763, XP009086445.

(Continued)

Primary Examiner — Carlos Azpuru
Assistant Examiner — Casey Hagopian
(74) Attorney, Agent, or Firm — Birch, Stewart, Kolasch & Birch, LLP

(57) ABSTRACT

Stable pharmaceutical composition consisting of a hydrosoluble vinflunine salt and at least one diluent and one lubricant, said composition being in the form of a solid intended for oral administration. The hydrosoluble vinflunine salt is preferably Vinflunine ditartrate. The pharmaceutical composition is advantageously in the form of a capsule or tablet. The invention also concerns a method of treating cancer pathology comprising the oral administration of the pharmaceutical composition of the invention.

22 Claims, No Drawings

(56) References Cited

OTHER PUBLICATIONS

Zhou et al., "Relative Bioavailability of Two Oral Formulations of Navelbine in Cancer Patients," Biopharmaceutics & Drug Disposition, vol. 15, 1994, pp. 577-586, XP009051771.

"Colloidal Silicon Dioxide," Handbook of Pharmaceutical Excipients, International Pharmaceutical Excipients Council Japan, Feb. 28, 2007, pp. 336-339.

"Croscarmellose Sodium," Pharmaceutical Excipients Dictionary, International Pharmaceutical Excipients Council Japan, 1994, pp. 46, 72, 73, 106, 107, 130 and 131.

"Microcrystalline Cellulose," Supplement to Pharmaceutical Excipients Dictionary, International Pharmaceutical Excipients Council Japan, 1995, p. 42.

* cited by examiner

STABLE PHARMACEUTICAL COMPOSITION COMPRISING A HYDROSOLUBLE VINFLUNINE SALT

This application is the National Phase of PCT/EP2008/058893 filed on Jul. 9, 2008, which claims priority under 35 U.S.C. 119(e) to U.S. Provisional Application No. 60/970,334 filed on Sep. 6, 2007, and under 35 U.S.C. 119(a) to Patent Application No. 0756421 filed in France on Jul. 11, 2007, all of which are hereby expressly incorporated by reference into the present application.

This invention relates to solid and stable pharmaceutical forms of hydrosoluble derivatives of Vinca alkaloids, and more particularly to vinflunine derivatives, namely vinflunine ditartrate, which are intended for oral administration.

Anti-cancer chemotherapy was initially developed using the intravenous methods. The arguments in favor of this administration route are:
  lesser gastrointestinal toxicity,
  total bioavailability, as well as
  potentially lower inter- and intra-patient exposure variations than by oral route.

However, the intravenous route has a number of serious disadvantages which limit its use: the morbidity of vein access, possible complications of the central vein channels (infection, thrombosis), the risk of extravasation.

For several years, oral forms of anti-cancer chemotherapy have been developed more and more because of the real benefit for the patient. Furthermore, pharmaco-economic considerations, which are becoming increasingly important in the choice of therapeutic strategies, are also leading towards the development of oral treatments.

Many exploratory studies have been conducted on the possible use of molecules intended for the treatment of cancer and administered by oral route, whether these are former active ingredients (for example: etoposide, cyclophosphamide and idarubicine), new synthetic derivatives of fluoropyrimidines (for example: UFT, capecitabine, S-1), derivatives of platinum (for example: JM-216) or Vinca alkaloids (for example: vinorelbine)

Vinflunine is an indole derivative of the vinblastine and vincristine family.

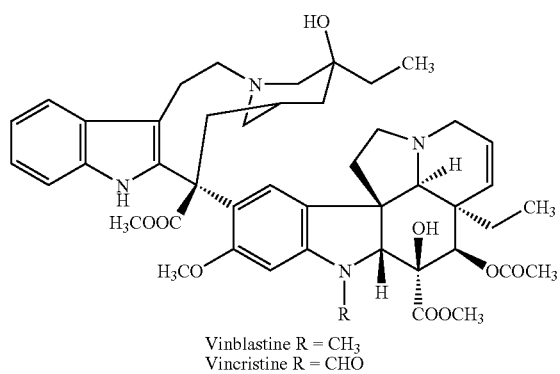

Vinblastine R = CH₃
Vincristine R = CHO

These compounds are antimitotic alkaloids, extracts of *Catharanthus roseus*, and have been used for many years in anti-cancer chemotherapy. The difficulty in obtaining these derivatives by extraction from plants has led several research groups to identify new similar substances with the same properties and to develop a procedure for producing them by hemisynthesis. In this way, vindesine and vinorelbine (Navelbine) have been produced and sold as cancer treatments. The principal feature of the chemical structure of these compounds is an association of two alkaloid monomers, catharanthine and vindoline.

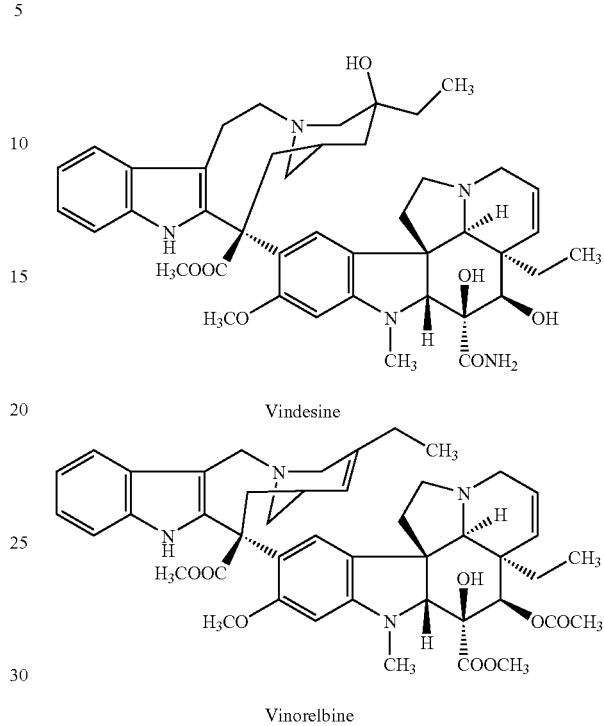

Vindesine

Vinorelbine

In the course of the development of new synthetic pathways to produce vinorelbine, the reactivity of this compound in a super-acid medium led to the identification of a new molecule 20',20'-difluoro-3',4'-dihydrovinorelbine, or vinflunine (WO95/03312). The therapeutic benefits of this compound were also verified in the course of the same research work.

The precise configuration of vinflunine has been studied by different $^1$H-NMR and $^{13}$C-NMR spectroscopy methods (Magn. Reson. Chem., 2001, 39, p. 43-48). This study was conducted on vinflunine ditartrate in solution. Nevertheless, this salt has hygroscopic properties which limit its stability in the solid state and constitute a handicap to industrial manufacturing. It has been isolated in the form of an amorphous powdery solid which has to be stored at negative temperatures (below −15° C.) and under an inert gas atmosphere, such as nitrogen or argon.

The handling and storage of this compound is therefore a delicate matter and any pharmaceutical form leading to an improvement in its physical stability in the solid state would simplify the manufacturing, storage and packaging processes.

There is currently an injectable form at an advanced stage of development (phase III trials). It has been decided that an oral form for home administration should be developed in order to improve patient compliance with treatment, which follows on from the injectable form and makes it possible to avoid days spent in hospital.

The solid form should achieve an absolute bioavailability of at least 50%, preferably equivalent to the solution form, in addition to low interindividual variability (below 30%). This type of active ingredient does in fact have a narrow therapeutic range, but which is still largely unknown and may vary from several dozens to several hundreds of milligrams.

In the choice of excipients, a compromise has to be found between the stability and bioavailability of the active ingredient. The excipients must protect the latter while not constituting an obstacle to its dispersal and rapid availability in the body.

Moreover, the risk to the individual's health and to the environment, due to the handling of cytotoxic compounds in powder form on the industrial scale, poses an additional problem that has to be overcome.

The aim of this invention is therefore to find a pharmaceutical form with a shelf life of at least 24 months under storage conditions not requiring freezing.

Oral forms of vinflunine ditartrate according to the present invention are solid forms consisting of conventional excipients for compression or for capsules (diluents, binders, flow agents, disintegrates, lubricants). Surprisingly, these forms are stable enough to be stored at 5° C. for 24 months in sealed packaging.

This invention therefore makes it possible to improve patient comfort, since the oral forms of the capsules and tablets according to the invention allow medication to be taken at home.

Moreover, solid oral forms such as capsules or tablets reduce production costs compared to technologies requiring the active ingredient to be kept in solution or in dispersion inside the pharmaceutical form (for example a soft capsule).

The oral forms according to the invention are solid forms made from mixtures of a hydrosoluble vinflunine salt, advantageously vinflunine ditartrate, and excipients. They consist of at least one diluent and one lubricant and can be obtained by means of several manufacturing procedures. These procedures are conventional industrial procedures for the manufacture of solid forms, known to the professional and therefore perfectly suited to industrial processing.

The manufacturing procedures for the compositions according to the invention can consist of a dry mixture of several compounds, followed by distribution in capsules or compression with a final tablet coating step.

Thus, in the case of making them by direct dry mixing, the active ingredient is, in a first phase, mixed with the diluent(s), optionally the disintegrant as well as the flow agent, in a standard mixer of the pharmaceutical industry such as a tumbler mixer for example. This premix is stirred at room temperature for about ten minutes until a homogenous mixture is obtained. Subsequently, the lubricant is added into the mixer before proceeding with lubrication by continuous stirring for about 5 to 10 further minutes. The thereby obtained mixture may be used for filling gelatine capsules with adequate equipment of the pharmaceutical industry. Alternatively said mixture may also be compressed on a press in order to obtain tablets. In the latter case, the obtained tablets may advantageously be submitted to a film-coating step.

Mixtures can also be granulated by wet or dry route prior to the lubrication step, and then distributed into capsules or tablets in the same way as above before being finally coated.

In the case of manufacture by wet granulation, the active ingredient is initially carefully mixed with the diluent and binder by means of a conventional mixer commonly used in the pharmaceutical industry. Advantageously, this mixing is carried out by means of a mixer-granulator-drier in order to avoid handling of the product in several pieces of equipment in view of the cytotoxic nature of the active ingredient.

Granulation as such can be carried out by addition of a granulation solvent. The granulation solvent can be aqueous, alcoholic or hydro-alcoholic.

In the case of an alcoholic solvent, ethanol is preferred as the alcoholic solvent and, in the case of a hydro-alcoholic solvent, a water/ethanol mixture in the weight ratio between 60/40 and 40/60 is used, and more particularly 50/50. In order to ensure maximum stability of the active ingredient both during the granulation step and during storage, an aqueous solvent, particularly water, is preferred.

The weight ratio of the granulation solvent to the quantity of mixture to be granulated should be between 10 and 25%, preferably between 15 and 22%. The mixture humidified in this way is combined and mixed in order to carry out granulation, that is to say agglomeration of the ingredients in the form of granules.

The granulated mixture then undergoes a drying step in order to obtain the dry pellet that is to say with humidity in the order of that corresponding to the mixture prior to granulation. Drying can be carried out inside the mixer-granulator-drier under vacuum in order to avoid overly high temperatures which damage the stability of the active ingredient. Alternatively, the granulated mixture can be dried in an oven placed under vacuum, with possible use of a fluidised air bed.

In a particular form of implementation of the procedure, the granules obtained are calibrated to a size between 100 and 250 μm, preferably around 200 μm An external phase consisting of a disintegrant and/or flow agent can be added to these granules obtained by wet route. These constituents are intimately mixed in a mixer such as a turning mixer.

The lubricant is then added to the mixer in order to obtain lubricated granules.

The lubricated granules can be put into capsules or compacted on a tablet press, using techniques known by those skilled in the art.

In the case of manufacturing by dry granulation, the active ingredient is intimately mixed with the diluent, possibly with the addition of a binder, in a pharmaceutical industry type mixer. The mixture is then granulated via a granulation step, without addition of a solvent, such as a briquetting or compacting step, in a roller compacter for example.

The agglomerates obtained in this manner can then undergo a grinding/calibration step in order to reduce their size and produce granules.

In a particular form of implementation of the procedure, the granules obtained are calibrated to a size between 100 and 250 μm, preferably around 200 μm An external phase consisting of a flow agent and/or disintegrant can be added to these granules obtained by wet route.

The granules obtained in this way are mixed with the lubricant for the time required to obtain uniform distribution of the lubricant on the granules.

In the same way as above, the lubricated granules can be put into capsules or compacted on a tablet press using techniques known to the professional.

Alternatively, the composition of the invention can be obtained by direct mixing by dry route, that is to say by carefully mixing the active ingredient with a diluent and, possibly, a disintegrant.

The lubricant and possibly the flow agent are added in the final step at the end of mixing, prior to distribution into capsules or compression into tablets.

The invention therefore relates more precisely to a stable pharmaceutical composition comprising a hydrosoluble vinflunine salt and at least one diluent and one lubricant, said composition being presented in solid form intended for oral administration.

The term <<stable>>, in the context of this invention, refers to a composition in which after storage, optionally under an inert atmosphere, for a duration of 24 months at a temperature of 0 to 10° C., advantageously of 2 to 8° C., has an impurity level of under 2%, advantageously under 1% and even more preferably under 0.5%.

The term <<diluent>>, in the context of this invention, refers to a substance that makes it possible to increase the weight of a pharmaceutical composition in order to ensure uniformity of mass and active ingredient content in the final pharmaceutical form, whether tablets or capsules. The diluents also ensure good flow of the mixture during the manufacturing process for active ingredients which do not flow well in general. They also facilitate compression in the course of the tablet manufacturing process.

The term <<lubricant>>, in the context of this invention, refers to a substance capable of reducing friction between the various constituents of the excipient mixture, in the form of a powder, and possibly containing the active ingredient. Lubricants make it possible to reduce adherence of the powder to the punch and matrix. They also lead to better transmission of compression forces. However, if added in excess, they reduce tablet cohesion.

The term <<binder>>, in the context of this invention, refers to a substance capable of interparticle bonds. Binders make it possible to reduce the compression force needed to produce the tablets. Some binders, such as cellulose derivatives, lead to the intertwining of the particles to be agglomerated. Others have a low melting point and are likely to form interparticle bridges during temperature increases in the course of the compression process.

The term <<flow agent>>, in the context of this invention, refers to a substance capable of improving the flow of a solid mixture, by improving the fluidity of the powder and, consequently, leading to uniform filling of the compression chamber.

The term <<disintegrant>>, in the context of this invention, refers to a substance which leads to crumbling of the pharmaceutical form in the presence of a liquid, for example in the stomach or on contact with digestive fluids, thus releasing the active ingredient.

The term <<film-forming agent>>, in the context of this invention, refers to a substance, usually polymeric, capable of coating the tablets and even the capsule tunic with a fine layer. It can play the role of a colouring agent or mask unpleasant odours. It can also protect patients and medical staff, at the manual and bucco-pharyngeal levels, against the toxicity of the active ingredient. It can also be gastroresistant or dialyzing. In this case, the term "coating agent" is used since the amount deposited is larger.

The term <<film-forming adjuvant>>, in the context of this invention, refers to plasticizing agents which make it possible to prevent the film layer from being too brittle. They can also make it possible to decrease the layer-forming temperature.

The term <<absolute bioavailability>>, in the context of this invention, refers to the ratio of active ingredient levels in the blood found after oral administration compared to intravenous administration.

The term <<interindividual variability>>, in the context of this invention, refers to the variations observed at a given moment between the plasma concentrations of the same active ingredient within a given population of people (healthy volunteers, patients, etc).

The diluent is advantageously chosen from the sugars, advantageously saccharose, fructose, glucose, polyols, advantageously mannitol, xylitol, sorbitol, maltitol, lactitol, polysaccharides, natural or pregelatinized starches, maltodextrins, cyclodextrins, mineral compounds, dihydrated or anhydrous dicalcium or tricalcium phosphate, cellulose derivatives, preferably microcrystalline cellulose, monohydrated or anhydrous lactoses, as well as mixtures thereof, and is more advantageously chosen from dihydrated dicalcium phosphate, mannitol, pregelatinized maize starch, microcrystalline cellulose and mixtures thereof.

The lubricant is advantageously chosen from fatty acid salts, advantageously magnesium stearate, aluminium stearate, calcium stearate, sodium stearate, sorbitan stearate, zinc stearate, fatty acid esters, advantageously glycerol behenate, glycerol monostearate, glycerol palmitostearate, stearic acid, stearyl alcohol, hydrogenated or non-hydrogenated ricin oils, hydrogenated vegetable oils, maize oil, sodium benzoate, talcum, sodium stearyl-fumarate, fatty acid triglycerides, polyethylene glycol and its derivatives as well as mixtures thereof, and is advantageously magnesium stearate.

The diluent advantageously consists of a mixture of microcrystalline cellulose and a compound chosen from D-mannitol, maize starch and dihydrated dicalcium phosphate.

The proportion of diluent is advantageously between 20 and 80% of the total weight of the composition, more advantageously between 30 and 60%, more advantageously equal to about 56% or 40% or 36%.

The proportion of lubricant is advantageously between 0.5 and 10% of the total weight of the composition, advantageously between 1 and 5%, more advantageously equal to about 1.5% or 2.5%.

The composition according to the invention can include a binder.

The binder can be chosen from cellulose derivatives, advantageously hydroxypropylmethylcellulose, hydroxypropylcellulose, hydroxyethylcellulose, methylcellulose, cellulose, from polyvinylpyrrolidone, gums, advantageously guar gum, adragante gum, gum arabic, xanthan gum, sugars, saccharose or glucose, gelatin, polyethylene glycol, or a vinylpyrrolidone and vinylacetate copolymer, as well as mixtures thereof and is more advantageously hydroxypropylmethylcellulose.

The proportion of binder is advantageously between 1 and 10% of the total weight of the composition, advantageously equal to about 5%.

The composition according to the invention can include a disintegrant.

The disintegrant is advantageously chosen from sodium carmellose, calcium carmellose, cellulose, starch derivatives preferably carboxymethyl starch, pregelatinized starches, natural starches, polyvinylpyrrolidone derivatives, advantageously crospovidone or copovidone, as well as mixtures thereof, and advantageously crospovidone, sodium carboxymethyl starch or sodium croscarmellose, and more advantageously still sodium croscarmellose.

The proportion of disintegrant is between 1 and 10% of the total weight of the composition, advantageously 2 and 8%, and more advantageously equal to about 5% or 7%.

The composition according to the invention can include a flow agent.

The flow agent is advantageously chosen from hydrophilic or hydrophobic colloidal silicas, hydrated or anhydrous, and is preferably a hydrophilic dihydrated colloidal silica.

The proportion of flow agent and/or lubricant is advantageously between 0.2 and 5% of the total weight of the composition, advantageously equal to about 1.75% or 2.25%.

According to an advantageous embodiment of the invention, the composition by weight is as follows:
- about 53% of diluent, advantageously about 32% of D-mannitol and 21% of microcrystalline cellulose, or advantageously about 32% of dihydrated calcium phosphate and 21% of microcrystalline cellulose;
- about 5% of binder, advantageously hydroxypropylmethylcellulose;

about 5% of disintegrant, advantageously sodium croscarmellose;
about 0.25% of flow agent, advantageously dihydrated colloidal silica;
about 1.5% of lubricant, advantageously magnesium stearate.

According to another advantageous embodiment of the invention, the composition by weight is as follows:
about 40% of diluent, advantageously about 24% of D-mannitol and 16% of microcrystalline cellulose;
about 5% of binder, advantageously hydroxypropylmethylcellulose;
about 5% of disintegrant, advantageously sodium croscarmellose;
about 0.25% of flow agent, advantageously dihydrated colloidal silica;
about 1.5% of lubricant, advantageously magnesium stearate.

According to yet another embodiment of the invention, the composition by weight is as follows:
about 36% of diluent, advantageously about 22% of D-mannitol and 14% of microcrystalline cellulose;
about 5% of binder, advantageously hydroxypropylmethylcellulose;
about 7% of disintegrant, advantageously sodium croscarmellose;
about 0.25% of flow agent, advantageously dihydrated colloidal silica;
about 2% of lubricant, advantageously magnesium stearate.

The composition of the invention can be in the form of a powder or granules.

Alternatively, the composition of the invention can be compacted into tablet form.

The composition of the invention in powder or granule form can be contained in a capsule made of a polymer, preferably chosen from gelatin, hydroxypropylmethylcellulose and pullulan.

The capsule can also include a colouring agent, advantageously chosen from pigments and oxides, as well as mixtures thereof, more advantageously chosen from titanium oxides and iron oxides and mixtures thereof.

A film-forming agent can be deposited on the surface of the tablet.

The film-forming agent is chosen from derivatives of cellulose, advantageously hydroxypropylmethylcellulose, hydroxyethylcellulose, hydroxypropylcellulose, methylcellulose, ethylcellulose, cellulose acetate, sodium carmellose, acrylic derivatives, advantageously poly butyl methacrylate, poly 2-dimethyl aminoethyl methacrylate, poly methyl methacrylate, poly ethyl acrylate, poly ethyl acrylate, trimethyl aminoethyl methacrylate chloride, cetyl alcohol, glycerol behenate, waxes, advantageously bees wax, Carnauba wax, gelatin, gum lac, cocoa oil, hydrogenated ricin oil, vinyl polyalcohol, polyvinylmethylether, vinyl polyacetate as well as mixtures thereof.

The proportion of film-forming agent is between 0.1 and 20% of the total weight of the composition, advantageously between 0.5 and 10%.

The composition according to the invention can include at least one film-forming adjuvant.

The film-forming adjuvant is advantageously chosen from polyoxyethylenes and alkyl ethers, plasticizers, advantageously triethylcitrate, dibutylsebacate, dibutylphthalate, mygliol, triacetine, loading agents, advantageously talcum, silica, titanium dioxide, coloring agents as well as mixtures thereof.

The proportion of film-forming adjuvant is between 0.01 and 5% of the total weight of the composition.

In an advantageous embodiment of the invention, the composition comprises by weight: about 0.19% of polyethylene glycol, 0.81% of titanium dioxide, 0.01% of quinoline yellow, 0.01% of red iron oxide.

The composition of the invention advantageously contains 5 to 80% of a hydrosoluble vinflunine salt, advantageously 20 to 60%.

When the composition of the invention is obtained by granulation, it advantageously contains by weight 30 to 50% of a hydrosoluble vinflunine salt, more advantageously about 35%.

When the composition of the invention is obtained by dry mixing, it advantageously contains by weight 35 to 55% of a hydrosoluble vinflunine salt, more advantageously about 50%.

The hydrosoluble vinflunine salt is advantageously vinflunine ditartrate.

The composition of the invention can advantageously be stored in sealed packaging in order to increase its stability.

The composition of the invention, compacted into tablets or contained in capsules, can thus be stored in sealed packaging, preferably in blister-packs coated with airtight and moisture-tight aluminized laminate or co-laminate according to the techniques known to professionals.

The invention also relates to a method for treating cancer comprising the oral administration of an effective amount of the pharmaceutical composition of the present invention to a patient in need thereof.

The invention will now be illustrated in a non-limiting manner by the following examples.

The tablets and capsules of the invention were prepared. Their stability and dissolution rate were measured. The bioavailability of the active ingredient was evaluated.

EXAMPLE NO 1

Two mixtures concentrated to about 35% of vinflunine ditartrate were prepared by wet granulation. An external phase (sodium croscarmellose, dihydrated colloidal silica) was then added prior to the lubrication step and distribution into capsules. The resulting capsules dosed at 20 and 75 mg of vinflunine base.

The main diluent is D-mannitol.

1.1. Unit and Centesimal Formulae of Granules

|  | A: Dosed at 20 mg | | B: Dosed at 75 mg | |
| --- | --- | --- | --- | --- |
| Constituents | Weight in mg | % | Weight in mg | % |
| Vinflunine ditartrate | 27.34 | 34.17 | 102.52 | 34.17 |
| D-mannitol | 26.12 | 32.65 | 97.95 | 32.65 |
| Microcrystalline cellulose | 17.14 | 21.42 | 64.27 | 21.42 |
| HPMC | 4.00 | 5.00 | 15.00 | 5.00 |
| Sodium croscarmellose | 4.00 | 5.00 | 15.00 | 5.00 |
| Dihydrated colloidal silica | 0.20 | 0.25 | 0.75 | 0.25 |
| Magnesium stearate | 1.20 | 1.50 | 4.50 | 1.50 |
| Total | 80.00 | 100.00 | 300.00 | 100.00 |
| Capsule size: 3 | 1 Capsule | / | / | / |
| Capsule size: 1 | / | / | 1 Capsule | / |

1.2. In Vitro Dissolution Tests

The amount of dissolved active ingredient was measured, using a standard European Pharmacopoeia protocol, in 1 liter of 0.1N HCl per capsule, at 37° C. with stirring at a speed of rpm. The results are reported in the table below. This operating method is also used in examples 2 to 6 below.

|  | Time (min) | | | | | |
| --- | --- | --- | --- | --- | --- | --- |
|  | 0 | 5 | 10 | 15 | 30 | 45 |
| Capsule A | | | | | | |
| Amount of dissolved active ingredient (%) | 0 | 72 | 89 | 99 | 100 | 100 |
| Capsule B | | | | | | |
| Amount of dissolved active ingredient (%) | 0 | 62 | 88 | 96 | 99 | 100 |

1.3. Stability Tests at 5° C. and 25° C. Under Sealed Conditions After 3 Months

The composition in the forms of capsule A and B were packaged in sealed packers. They were stored for 3 months at 5° C. at an external humidity level of 20%, or at 25° C. at an external humidity level of 60%.

The weight content in impurities (in % of the total weight of the composition) was assayed immediately after storage, then after 3 months of storage. The difference between these two percentages gives the change in impurity content.

It is compared to that obtained for freeze-dried vinflunine ditartrate stored under the same conditions.

The results are reported in the table below.

|  | Vinflunine ditartrate | Capsule A | Capsule B |
| --- | --- | --- | --- |
| Changes in impurity levels at 5° C. | +0.8 | +0.2 | +0.2 |
| Changes in impurity levels at 25° C. | +1.9 | +1.0 | +1.1 |

1.4. Bioavailability Study

The clinical study on bioavailability was carried out on batches A and B described above.

The oral bioavailability of the active ingredient in capsule form was compared with that of the active ingredient in a soft gelatin capsule form, filled with a 20% solution (w/w base vinflunine) of vinflunine ditartrate in propylene glycol.

The study was conducted on 20 patients who received a dose of 120 mg/m$^2$ of body area.

The results are reported in the table below.

|  | Absolute bioavailability | Interindividual variability |
| --- | --- | --- |
| Capsule | 57.3% | 19% |
| Soft capsule | 58.4% | 24% |

EXAMPLE NO 2

Two mixtures concentrated to about 35% of vinflunine ditartrate were prepared by wet granulation. An external phase (sodium croscarmellose, dihydrated colloidal silica) was then added prior to the lubrication step and distribution into capsules. The resulting capsules dosed at 20 and 75 mg of vinflunine base.

The main diluent is dihydrated dicalcium phosphate.

2.1. Unit and Centesimal Formulae of Granules

|  | Dosed at 20 mg | | Dosed at 75 mg | |
| --- | --- | --- | --- | --- |
| Constituents | Weight in mg | % | Weight in mg | % |
| Vinflunine ditartrate | 27.34 | 34.17 | 102.52 | 34.17 |
| Dihydrated dicalcium phosphate | 26.12 | 32.65 | 97.95 | 32.65 |
| Microcrystalline cellulose | 17.14 | 21.42 | 64.27 | 21.42 |
| HPMC | 4.00 | 5.00 | 15.00 | 5.00 |
| Sodium croscarmellose | 4.00 | 5.00 | 15.00 | 5.00 |
| Dihydrated colloidal silica | 0.20 | 0.25 | 0.75 | 0.25 |
| Magnesium stearate | 1.20 | 1.50 | 4.50 | 1.50 |
| Total | 80.00 | 100.00 | 300.00 | 100.00 |
| Capsule size: 3 | 1 Capsule | / | / | / |
| Capsule size: 1 | / | / | 1 Capsule | / |

2.1. In Vitro Dissolution Tests

|  | Time (min) | | | | | |
| --- | --- | --- | --- | --- | --- | --- |
|  | 0 | 5 | 10 | 15 | 30 | 45 |
| Dosed at 20 mg | | | | | | |
| Amount of dissolved active ingredient (%) | 0 | 80 | 94 | 98 | 99 | 100 |
| Dosed at 75 mg | | | | | | |
| Amount of dissolved active ingredient (%) | 0 | 66 | 88 | 96 | 99 | 100 |

EXAMPLE NO 3

A mixture concentrated to about 50% of vinflunine ditartrate was prepared by wet granulation. An external phase (sodium croscarmellose, dihydrated colloidal silica) was then added prior to the lubrication step and distribution into capsules. The resulting capsules dosed at 100 mg of vinflunine base.

The main diluent is D-mannitol.

3.1. Unit and Centesimal Formulae of Granules

|  | Dosed at 100 mg | |
| --- | --- | --- |
| Constituents | Weight in mg | % |
| Vinflunine ditartrate | 136.70 | 48.80 |
| D-mannitol | 66.24 | 23.65 |
| Microcrystalline cellulose | 44.16 | 15.80 |
| HPMC | 14.00 | 5.00 |
| Sodium croscarmellose | 14.00 | 5.00 |
| Dihydrated colloidal silica | 0.70 | 0.25 |
| Magnesium stearate | 4.20 | 1.50 |
| Total | 280.00 | 100.00 |
| Capsule size: 1 | 1 Capsule | / |

3.2. In Vitro Dissolution Tests

|  | Time (min) | | | | | |
| --- | --- | --- | --- | --- | --- | --- |
|  | 0 | 5 | 10 | 15 | 30 | 45 |
| Amount of dissolved active ingredient (%) | 0 | 22 | 39 | 57 | 96 | 99 |

EXAMPLE NO 4

A mixture concentrated to about 52% of vinflunine ditartrate was prepared using dry mixing prior to a lubrication step and distribution into capsules. The resulting capsules dosed at 90 mg of vinflunine base.

The main diluent is D-mannitol.

4.1. Unit and Centesimal Formulae of Granules

|  | Dosed at 90 mg | |
| --- | --- | --- |
| Constituents | Weight in mg | % |
| Vinflunine ditartrate | 123.03 | 52.35 |
| D-mannitol | 56.96 | 24.25 |
| Microcrystalline cellulose | 37.97 | 16.15 |
| Sodium croscarmellose | 11.75 | 5.00 |
| Dihydrated colloidal silica | 0.59 | 0.25 |
| Magnesium stearate | 4.70 | 2.00 |
| Total | 235.00 | 100.00 |
| Capsule size: 1 | 1 Capsule | / |

4.2. In Vitro Dissolution Tests

|  | Time (min) | | | | | |
| --- | --- | --- | --- | --- | --- | --- |
|  | 0 | 5 | 10 | 15 | 30 | 45 |
| Amount of dissolved active ingredient (%) | 0 | 82 | 100 | 100 | 100 | 100 |

EXAMPLE NO 5

A mixture concentrated to about 35% of vinflunine ditartrate was prepared by wet granulation. An external phase (sodium croscarmellose, dihydrated colloidal silica) was then added prior to compression and lubrication. The resulting capsules dosed at 20 mg of vinflunine base.

The main diluent is D-mannitol.

5.1. Unit and Centesimal Formulae of Granules

|  | Dosed at 20 mg | |
| --- | --- | --- |
| Constituents | Weight in mg | % |
| Vinflunine ditartrate | 27.34 | 34.17 |
| D-Mannitol | 26.44 | 32.65 |
| Microcrystalline cellulose 101 | 17.62 | 21.42 |
| HPMC | 5.52 | 5.00 |
| Sodium croscarmellose | 4.00 | 5.00 |
| Dihydrated colloidal silica | 0.20 | 0.25 |
| Magnesium stearate | 0.40 | 1.50 |
| Film | / | / |
| Macrogol 400P | 0.152 | 18.22 |
| Titanium dioxide | 0.66 | 79.14 |
| Spectracol quinoline yellow LK | 0.012 | 1.44 |
| Spectracol red iron oxide | 0.01 | 1.20 |
| Total | 82.35 | 100.00 |

5.2. In Vitro Dissolution Tests

|  | Time (min) | | | | | |
| --- | --- | --- | --- | --- | --- | --- |
|  | 0 | 5 | 10 | 15 | 30 | 45 |
| Amount of dissolved active ingredient (%) | 0 | 34 | 66 | 87 | 99 | 99 |

EXAMPLE NO 6

A mixture concentrated to about 48% of vinflunine ditartrate were prepared by wet granulation. An external phase (sodium croscarmellose, dihydrated colloidal silica) was then added prior to lubrication and compression. The resulting capsules dosed at 200 mg of vinflunine base.

The main diluent is D-mannitol.

6.1. Unit and Centesimal Formulae of Granules

|  | Dosed at 200 mg | |
| --- | --- | --- |
| Constituents | Weight in mg | % |
| Vinflunine ditartrate | 273.40 | 48.82 |
| D-Mannitol | 122.40 | 21.86 |
| Microcrystalline cellulose | 81.60 | 14.57 |
| HPMC | 28.00 | 5.00 |
| Sodium croscarmellose | 42.00 | 7.50 |
| Dihydrated colloidal silica | 1.40 | 0.25 |
| Magnesium stearate | 11.20 | 2.00 |
| Total | 560.00 | 100.00 |

6.2. In Vitro Dissolution Tests

|  | Time (min) | | | | | |
| --- | --- | --- | --- | --- | --- | --- |
|  | 0 | 5 | 10 | 15 | 30 | 45 |
| Amount of dissolved active ingredient (%) | 0 | 22 | 39 | 57 | 96 | 99 |

The experiments described above demonstrate that the compositions of the invention are stable at 5° C. in sealed packaging for 3 months.

The exceptionally high stability at 25° C. found for these compositions over a period of 3 months allows a shelf-life of 24 months at 5° C. to be envisaged.

The compositions of the invention release over 80% of the active ingredient in vitro in less than 30 minutes.

Moreover, they also show an absolute bioavailability and interindividual variability similar to those of an oral liquid form.

EXAMPLE NO. 7

A mixture with a 34.175% concentration of vinflunine ditartrate was prepared by dry mixing, before a step for lubrication and distribution in gelatin capsules.

Vinflunine ditartrate is incorporated into the diluents (D-mannitol and microcrystalline cellulose), to the disintegrant (sodium croscarmellose) and to the flow agent (colloidal silica dihydrate) in a mixer and preferentially a tumbler mixer. Mixing is carried out during a period for obtaining a homogenous mixture of the different components, this duration is preferentially 10 minutes. The mixing step is followed by a lubrication step carried out by the same mixer with magnesium stearate as lubricant. The duration of this step for obtaining optimum lubrication of the mixture is preferentially 5 minutes. The lubrication step is followed by distributing the mixture into gelatine capsules. The obtained gelatine capsules are dosed with 20 mg of vinflunine base.

7.1. Unitary and Centesimal Formulations of the Gelatine Capsules

| Components | 90 mg dosage | |
|---|---|---|
| | Weight in mg | % |
| Vinflunine ditartrate | 27.34 | 34.175 |
| D-mannitol | 27.88 | 34.850 |
| Microcrystalline cellulose | 18.58 | 19.475 |
| Sodium croscarmellose | 4.00 | 5.000 |
| Colloidal silica dihydrate | 0.20 | 0.250 |
| Magnesium stearate | 2.00 | 2.500 |
| Total | 80.00 | 100.000 |
| Gelatin capsule of size 3 | 1 gelatin capsule | / |

7.2. In Vitro Dissolution Tests

| | Time (min) | | | | | |
|---|---|---|---|---|---|---|
| | 0 | 5 | 10 | 15 | 30 | 45 |
| Amount of dissolved active ingredient (%) | 0 | 94 | 99 | 100 | 100 | 100 |

EXAMPLE NO. 8

A mixture with a vinflunine ditartrate concentration of about 51.265% was prepared by dry mixing, before a step for lubrication and distribution in gelatin capsules. Vinflunine ditartrate is incorporated into the diluents (D-mannitol and microcrystalline cellulose), to the disintegrant (sodium croscarmellose) and to the flow agent (colloidal silica dihydrate) in a mixer and preferentially a tumbler mixer. Mixing is carried out during a period for obtaining a homogenous mixture of the different components, this duration is preferentially 10 minutes. The mixing step is followed by a lubrication step carried out by the same mixer with magnesium stearate as lubricant. The duration of this step for obtaining optimum lubrication of the mixture is preferentially 5 minutes. The lubrication step is followed by distributing the mixture into gelatine capsules. The obtained gelatine capsules are dosed with 75 mg of vinflunine base.

8.1. Unitary and Centesimal Formulations of the Gelatine Capsules

| Components | 75 mg dosage | |
|---|---|---|
| | Weight in mg | % |
| Vinflunine ditartrate | 102.53 | 51.265 |
| D-mannitol | 49.18 | 24.590 |
| Microcrystalline cellulose | 32.79 | 16.395 |
| Sodium croscarmellose | 10.00 | 5.000 |
| Colloidal silica dihydrate | 0.50 | 0.250 |
| Magnesium stearate | 5.00 | 2.500 |
| Total | 200.00 | 100.000 |
| Gelatin capsule of size 1 | 1 gelatin capsule | / |

8.2. In Vitro Dissolution Tests

| | Time (min) | | | | | |
|---|---|---|---|---|---|---|
| | 0 | 5 | 10 | 15 | 30 | 45 |
| Amount of dissolved active ingredient (%) | 0 | 94 | 99 | 100 | 100 | 100 |

The invention claimed is:

1. A stable pharmaceutical composition comprising a hydrosoluble vinflunine ditartrate salt and at least one diluent, at least one binder, at least one disintegrant and at least one lubricant, said composition being presented in solid form intended for oral administration wherein
   the stable pharmaceutical composition contains 35 to 55% by weight of the hydrosoluble vinflunine ditartrate salt,
   the proportion of diluent is between 20 and 60% of the total weight of the composition,
   the proportion of the lubricant is between 1 and 5% of the total weight of the composition, and
   the proportion of the disintegrant is between 2 and 8% of the total weight of the composition, and
   wherein the composition is stable for over a period of 3 months allowing a shelf-life of about 24 months at 5° C.

2. The composition according to claim 1 wherein the diluent is chosen from sugars, polyols, polysaccharides, mineral compounds and mixtures thereof.

3. The composition according to claim 1 wherein the lubricant is chosen from fatty acid salts, fatty acid esters, hydrogenated or non-hydrogenated ricin oils, hydrogenated vegetable oils, maize oil, sodium benzoate, talcum, sodium stearyl-fumarate, fatty acid triglycerides, polyethylene glycol and its derivatives, as well as mixtures thereof.

4. The composition according to claim 1 wherein the diluent consists of a mixture of microcrystalline cellulose and a compound chosen from D-mannitol, maize starch and dihydrated dicalcium phosphate.

5. The composition according to claim 1 wherein the proportion of diluent is between 30 and 60% of the total weight of the composition.

6. The composition according to claim 1 wherein the binder is chosen from cellulose derivatives, cellulose, polyvinylpyrrolidone, sugars, gelatin, polyethylene glycol, or a vinylpyrrolidone and vinylacetate copolymer, and mixtures thereof.

7. The composition according to claim 1 wherein the proportion of binder is equal to about 5% of the total weight of the composition.

8. The composition according to claim 1 wherein the disintegrant is chosen from sodium carmellose, calcium carmellose, cellulose, starch derivatives, natural starches, polyvinylpyrrolidone derivatives, as well as mixtures thereof.

9. The composition according to claim 1 further comprising a flow agent.

10. The composition according to claim 9 wherein the flow agent is chosen from hydrophilic or hydrophobic colloidal silicas, hydrated or anhydrous.

11. The composition according to claim 9 wherein the total proportion of flow agent is between 0.2 and 5% of the total weight of the composition.

12. The composition according to claim 9 wherein it contains by weight:
- about 53% of diluent;
- about 5% of binder;
- about 5% of disintegrant;
- about 0.25% of flow agent;
- about 1.5% of lubricant.

13. The composition according to claim 9 wherein it contains by weight:
- about 40% of diluent;
- about 5% of binder;
- about 5% of disintegrant;
- about 0.25% of flow agent;
- about 1.5% of lubricant.

14. The composition according to claim 9 wherein it contains by weight:
- about 36% of diluent;
- about 5% of binder;
- about 7% of disintegrant;
- about 0.25% of flow agent;
- about 2% of lubricant.

15. The composition according to claim 1 in the form of a powder or granules.

16. The composition according to claim 1 compacted into tablets.

17. The composition according to claim 15 distributed into polymer capsules.

18. A method for treating cancer comprising the oral administration of an effective amount of the pharmaceutical composition of claim 1 to a patient in need thereof.

19. The composition of claim 2, wherein the sugars are selected from the group consisting of cyclodextrins, monohydrated or anhydrous lactoses, and mixtures thereof.

20. The composition of claim 6, wherein the sugars are selected from the group consisting of saccharose or glucose, or mixtures thereof.

21. The composition according to claim 2, wherein the mineral compounds are selected from the group consisting of dihydrated dicalcium phosphate, anhydrous dicalcium phosphate, tricalcium phosphate, and mixtures thereof.

22. The composition of claim 2, wherein the polysaccharides are selected from the group consisting of natural or pregelatinized starches, maltodextrins, cellulose derivatives, and mixtures thereof.

* * * * *